United States Patent
Pfrengle

(10) Patent No.: US 6,747,033 B2
(45) Date of Patent: Jun. 8, 2004

(54) FUNGICIDAL TRIAZOLOPYRIMID-7-YLIDENEAMINES

(75) Inventor: Waldemar Pfrengle, Seibersbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/879,258

(22) Filed: Jun. 12, 2001

(65) Prior Publication Data

US 2003/0083328 A1 May 1, 2003

(Under 37 CFR 1.47)

Related U.S. Application Data

(60) Provisional application No. 60/211,168, filed on Jun. 13, 2000.

(51) Int. Cl.$^7$ .................. C07D 487/04; A01N 43/90
(52) U.S. Cl. .................. 514/259.3; 544/263; 544/229
(58) Field of Search .............. 514/259.31; 544/263, 544/229

(56) References Cited

U.S. PATENT DOCUMENTS

| | | | |
|---|---|---|---|
| 3,868,361 A | 2/1975 | Tolman et al. | 260/211.5 |
| 5,593,996 A | 1/1997 | Pees et al. | 514/258 |
| 5,817,663 A | 10/1998 | Pees et al. | 544/263 |
| 5,948,783 A | 9/1999 | Pees et al. | 514/258 |
| 5,981,534 A | 11/1999 | Pfrengle | 514/258 |
| 5,985,883 A | 11/1999 | Pees | 514/258 |
| 5,994,360 A | 11/1999 | Pfrengle | 514/258 |
| 6,117,876 A | 9/2000 | Pees et al. | 514/258 |

FOREIGN PATENT DOCUMENTS

| | | | |
|---|---|---|---|
| EP | 0 550 113 | 7/1993 | C07D/487/04 |
| EP | 0 834 513 | 4/1998 | C07D/487/04 |
| FR | 2765875 | 1/1999 | C07D/487/04 |
| WO | 98/46607 | 10/1998 | C07D/487/04 |
| WO | 98/46608 | 10/1998 | C07D/487/04 |
| WO | 99/48893 | 9/1999 | C07D/487/04 |

Primary Examiner—Mark L. Berch
(74) Attorney, Agent, or Firm—Keil & Weinkauf

(57) ABSTRACT

Compounds of formula I

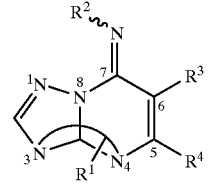

in which $R^1$ is alkyl, alkoxyalkyl, cycloalkylalkyl, alkenyl, alkynyl, alkadienyl, haloalkyl, trihydrocarbylsilyl, formyl, alkanoyl or alkoxycarbonyl group being attached either to the nitrogen in the 3- or 4-position;

$R^2$ is hydrogen, alkyl, alkenyl, alkynyl, alkadienyl, haloalkyl, cycloalkyl, bicycloalkyl, phenyl, naphthyl, 5- or 6-membered heteroaryl or heterocyclic groups containing one to four nitrogen atoms or one to three nitrogen atoms and one sulfur or oxygen atom as ring members;

$R^3$ is phenyl, cycloalkyl or 5- or 6-membered heteroaryl containing besides carbon atoms one to four nitrogen atoms or one to three nitrogen atoms and one sulfur or oxygen atom as ring members;

$R^4$ is halogen, amino, alkoxy, haloalkoxy, alkylamino or dialkylamino;

wherein the bent line indicates that the double Bond may be located between the 3- and 9-position or the 4- and 9-Position; and the zigzag line ⌇ indicates that the groups connected may have the (E)- or (Z)-configuration;

$R^1$ to $R^4$ groups may be unsubstituted or substituted as defined in the description;

processes for preparing these compounds, constituents comprising them and their use for controlling harmful fungi are described.

10 Claims, No Drawings

FUNGICIDAL TRIAZOLOPYRIMID-7-YLIDENEAMINES

This application claims the benefit under 35 USC 119(e) of provisional application 60/211,168 filed Jun. 13, 2000.

The present invention provides compounds of formula I

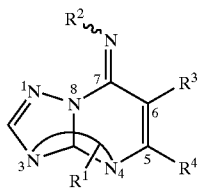

in which

R$^1$ is C$_1$–C$_{10}$-alkyl, C$_1$–C$_6$-alkoxy-C$_1$–C$_6$-alkyl, C$_3$–C$_8$-cycloal-kyl-C$_1$–C$_6$-alkyl, C$_2$–C$_{10}$-alkenyl, C$_2$–C$_{10}$-alkynyl, C$_4$–C$_{10}$-alka-dienyl, C$_1$–C$_{10}$-haloalkyl, trihydrocarbylsilyl, formyl, C$_1$–C$_{10}$-alkanoyl or C$_1$–C$_{10}$-alkoxycarbonyl group being attached either to the nitrogen in the 3- or 4-position;

R$^2$ is hydrogen, C$_1$–C$_{10}$-alkyl, C$_2$–C$_{10}$-alkenyl, C$_2$–C$_{10}$-alkynyl, C$_4$–C$_{10}$-alkadienyl, C$_1$–C$_{10}$-haloalkyl, C$_3$–C$_6$-cycloalkyl, C$_8$–C$_{14}$-bicycloalkyl, phenyl, naphthyl, 5- or 6-membered heteroaryl or heterocyclic groups containing one to four nitrogen atoms or one to three nitrogen atoms and one sulfur or oxygen atom as ring members;

R$^3$ is phenyl, C$_3$–C$_6$-cycloalkyl or 5- or 6-membered heteroaryl containing besides carbon atoms one to four nitrogen atoms or one to three nitrogen atoms and one sulfur or oxygen atom as ring members;

R$^4$ is halogen, amino, C$_1$–C$_{10}$-alkoxy, C$_1$–C$_{10}$-haloalkoxy, C$_1$–C$_{10}$-alkylamino or di-C$_1$–C$_{10}$-alkylamino;

wherein the bent line indicates that the double Bond may be located between the 3- and 9-position or the 4- and 9-Position; and the zigzag line  indicates that the groups connected may have the (E)- or (Z)-configuration;

R$^1$ to R$^4$ groups independently from one another may be unsubstituted or substituted by one to three groups R$^a$:

R$^a$ halogen, nitro, cyano, hydroxy, C$_1$–C$_6$-alkyl, C$_3$–C$_6$-cycloalkyl, C$_3$–C$_6$-cycloalkenyl, C$_1$–C$_6$-haloalkyl, C$_3$–C$_6$-halocycloalkyl, C$_1$–C$_6$-alkoxy, C$_1$–C$_6$-haloalkoxy, tri-C$_1$–C$_4$-alkylsilyl, phenyl, halo- or dihalo-phenyl or pyridyl;

It is an object of the present invention to provide fungicidal active compounds.

Moreover, the invention relates to processes for preparing these compounds, to compositions comprising them and to their use for controlling harmful fungi.

Fungicidal 7-amino-triazolopyrimidines are disclosed for example by U.S. Pat. No. 5,593,996, WO-A 98/14608, FR-A 2,765,875 and WO-A 99/48893.

It is an object of the present invention to provide compounds having improved activity.

We have found that this object is achieved by the compounds defined at the outset. Furthermore, we have found processes for their preparation, compositions comprising them and methods for controlling animal pests and harmful fungi using the compounds I.

The present invention further provides a process for the preparation of a compound of formula I as defined above which comprises treating a compound of formula II:

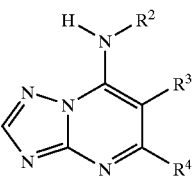

in which R$^2$ through R$^4$ are as defined in claim 1;

with an alkylation agent of formula III:

R$^1$—X     III in which R$^1$ is as defined in formula I and X represents a nucleophilic exchangeable leaving group, preferably a halogen atom, in particular a bromine or iodine atom, in the presence of a weak base or a buffer system.

Compounds of formula II are known for example from U.S. Pat. No. 5,593,996, WO 98/14608, FR-A 2,765,875 or WO-A 99/48893.

The reaction between the triazolopyrimidines of formula II, the weak base and the alkylating agent of formula III is preferably carried out in the presence of an inert solvent. Suitable solvents include ethers, such as dioxane, diethyl ether and tetrahydrofuran, halogenated hydrocarbons such as dichloromethane, amides, such as dimethylformamide or N-methylpyrrolidone and aromatic hydrocarbons, for example toluene or mixtures of these solvents.

The reaction is suitably carried out at a temperature in the range from −78° C. to 100° C., the preferred reaction temperature is from 10° C. to 80° C., particular at ambient temperature. Suitable weak bases include tertiary amines such as triethylamine or pyridine, metal carbonates such as sodium carbonate or carbonate or metal hydrogencarbonates such as sodium hydrogencarbonate or potassium hydrogencarbonate.

In the symbol definitions given in the formulae above, collective terms were used which generally represent the following substituents:

The term halogen atom may denote a bromine; iodine, chlorine or fluorine atom, and is especially a bromine, chlorine or fluorine atom, in particular a fluorine or chlorine atom.

The terms alkyl, alkenyl, alkynyl, alkadienyl, haloalkyl as used herein with respect to a radical or moiety refer to a straight or branched chain radical or moiety. Such radicals have up to 10, in particular up to 6 carbon atoms. Suitably an alkyl moiety has from 1 to 6 carbon atoms, preferably from 1 to 4 carbon atoms. A preferred alkyl moiety is an ethyl or especially a methyl group. Suitably an alkenyl moiety has from 2 to 6 carbon atoms. A preferred alkenyl moiety is allyl or especially a 2-methylallyl group. Suitably a haloalkyl moiety has from 1 to 6 fluorine atoms. A preferred haloalkyl moiety is the 2,2,2-trifluoroethyl or 1,1,1-trifluoroprop-2-yl group.

The term heteroaryl, as used herein with respect to a radical or moiety refers to a heteroaryl group having 5 or 6 ring atoms selected from carbon, nitrogen, oxygen and sulfur, at least one of which being nitrogen, oxygen or sulfur, in particular pyridyl, pyrimidyl, pyrazolyl or thienyl.

The term cycloalkyl, as used herein which respect to a radical or moiety refers to a cycloalkyl group having 3 to 8 carbon atoms, preferably 5 to 7 carbon atoms, in particular cyclopentyl being optionally substituted by one or more halogen atoms, nitro, cyano, alkyl, preferably C$_1$–C$_6$-alkyl, alkoxy, preferably C$_1$–C$_6$-alkoxy.

The term heterocyclyl, as used herein with respect to a radical or moiety refers to a saturated heterocyclyl group having 5 or 6 ring atoms selected from carbon, nitrogen, oxygen and sulfur, at least one of which being-nitrogen, oxygen or sulfur being optionally substituted by one or more halogen atoms, nitro, cyano, $C_1$–$C_6$-alkyl, $C_1$–$C_6$-alkoxy, in particular pyrrolodinyl, pyrazolidinyl, piperidinyl, piperazinyl or morpholin-4-yl.

The term trihydrocarbylsilyl, as used herein which respect to a radical or moiety refers to a silyl group which is substituted by three alkyl and/or phenyl groups. Most preferred are trimethylsilyl, triethylsityl, tert.-butyldimethylsilyl and tert.-butyl-di-phenylsilyl.

The invention especially relates to compounds of formula I in which any alkyl or haloalkyl part of the groups $R^1$, $R^2$, $R^3$ or $R^4$, which may be straight chained or branched, contains preferably 1 to 9 carbon atoms, mores preferably 2 to 6 carbon atoms, any alkenyl, alkadienyl or alkynyl part of the substituents $R^1$ or $R^2$ contains preferably 2 to 9 carbon atoms, more preferably 3 to 6 carbon atoms, any cycloalkyl part of the substituent $R^1$ contains preferably from 3 to 8 a carbon atoms, more preferably from 3 to 6 carbon atoms. Any alkyl, alkenyl, alkadienyl or alkynyl group may be linear or branched. A 5- to 6-membered heterocyclic group may be any heterocyclic group with 5 to 6 ring atoms, interrupted by one or mores heteroatoms selected from sulfur, nitrogen, and oxygen, preferably oxygen.

The invention especially relates to compounds of the general formula I in which $R^1$ represents a straight-chained or branched $C_1$–$C_{10}$-alkyl, in particular a straight-chained $C_1$–$C_6$-alkyl group, a $C_3$–$C_8$-cycloalkyl-$C_1$–$C_6$-alkyl, $C_1$–$C_{10}$-alkoxy-$C_1$–$C_6$-alkyl or a $C_1$–$C_{10}$-haloalkyl group.

The invention especially relates to compounds of the general formula I in which $R^2$ represents a straight-chained or branched $C_1$–$C_{10}$-alkyl, in particular a branched $C_3$–$C_6$-alkyl group, a $C_3$–$C_8$-cycloalkyl, a $C_3$–$C_8$-cycloalkyl-$C_1$–$C_6$-alkyl, $C_1$–$C_{10}$-alkoxy-$C_1$–$C_6$-alkyl, a $C_1$–$C_{10}$-haloalkyl or a phenyl group being optionally substituted by one to three halogen atoms or $C_1$–$C_{10}$-alkyl or $C_1$–$C_{10}$-alkoxy groups.

Included in the scope of the present invention are (R) and (S) isomers of compounds of general formula I having a chiral center and the racemates thereof, and salts, N-oxides and acid addition compounds.

With respect to their intended use, preference is given to compounds of formula I having the following substituents, where the preference is valid in each case on its own or in combination:

$R^1$ most preferably is a $C_1$–$C_6$-alkyl group.

Compounds of formula I are preferred wherein $R^1$ is in 3- or 4-position and denotes methyl, ethyl or n- or iso-propyl.

$R^2$ most preferably denotes a $C_1$–$C_{10}$-haloalkyl group, in particular a polyfluorinated alkyl group, most preferred a 2,2,2-trifluoroethyl, a 2-(1,1,1-trifluoropropyl) or a 2-(1,1,1-trifluorobutyl) group or an optionally substituted $C_3$–$C_1$-cycloalkyl group, preferably a cyclopentyl or cyclohexyl group.

Compounds of formula I are preferred wherein $R^3$ is phenyl optionally substituted by one or more fluorine and/or chlorine atoms and/or methoxy groups.

Compounds of formula 1 are particularly preferred in which $R^3$ represents a phenyl group being substituted by 2 or 3 substituents. Most preferred at least one of these substituents is attached in the 2-position with respect to the point of attachment to the pyrimidine moiety. Such substituents preferably include a halogen atoms or $C_1$–$C_6$-alkoxy groups.

Moreover, compounds of formula I are particularly preferred in which $R^3$ is an optionally substituted phenyl group of formula:

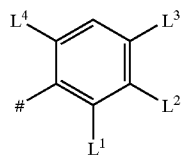

wherein # denotes the bond to the triazolopyrimidine ring and $L^1$ through $L^4$ each independently are hydrogen, fluorine or chlorine or methoxy, in particular wherein $L^1$ is fluorine or chlorine, $L^2$ and $L^4$ each independently are hydrogen or fluorine or chlorine, $L^3$ is hydrogen or fluorine or chlorine or methoxy.

Compounds of formula I in which $R^4$ represents a halogen atom, in particular a chlorine atom are particularly preferred.

Most preferred are the compounds of formula IA

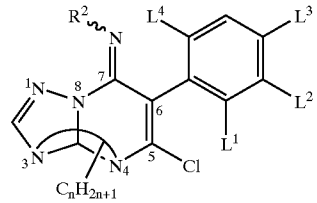

IA in which $R^2$ has the meaning given for formula I, $L^1$ represents halogen and $L^3$ and $L^4$ each independently represent hydrogen, halogen or alkoxy, and n represents an integer from 1 to 10.

Especially preferred are following compounds of formula I:

N-[5-chloro-4-methyl-S-(2,4,6-trifluorophenyl)-4H-[1,2,4)triazolo[1,5-α]pyrimidin-7-ylidene]-N-(2,2,2-trifluoroethyl)-amine, N-[5-chloro-4-methyl-6-(2,4,6-trifluorophenyl)-4H-[1,2,4]triazolo[1,5-α]pyrimidin-7-ylidene]-N-cyclopentyl-amine, N-[5-chloro-4-methyl-6-(2,4,6-trifluorophenyl)-4H-[1,2,4]triazolo[1,5-α]pyrimidin-7-ylidene]-N-(1,1,1)-trifluoroprop-2-yl)-amine, N-[5-chloro-4-methyl-6-(2,4,6-trifluorophenyl)4H-(1,2,4]triazolo[1,5-α]pyrimidin-7-ylidene]-N-isopropyl-amine, N-sec-butyl-N-[

5-chloro-4-methyl-6-(2,4,6-trifluorophenyl)-4H-[1,2,4]triazolo[1,5-α]pyrimidin-7-ylidene]-amine, N-bicyclo[2.2.1]hept-2-yl-N-(5-chloro-4-methyl-6-(2,4,6-trifluorophenyl)-4H-[1,2,4]triazolo[1,5-α,]pyrimidin-7-ylidene]-amine, N-[5-chloro-6-(2-chloro-6-fluorophenyl)-4-methyl-4H-(1,2,4]triazolo[1,5-α]pyrimidin-7-ylidene]-N-cyclopentyl-amine, N-[5-chloro-6-(2-chloro-6-fluorophenyl)-4-methyl-4H-[1,2,4]triazolo[1,5-α]pyrimidin-7-ylidene]-N-(2,2,2-trifluoroethyl)-amine, N-[5-chloro-6-(2-chloro-G-fluoro-phenyl)-4-methyl-4H-[1,2,4]triazolo[1,5-α]pyrimidin-7-ylidene]-N-(1,1,1-trifluoroprop-2-yl)-amine, N-[5-chloro-6-(2-chloro-6-fluoro-phenyl)-4-methyl-4H-[1,2,4]triazolo[1,5-α]pyrimidin-7-ylidene]-N-isopropyl-amine, N-sec-butyl-N-[5-chloro-6-(2-chloro-6-fluorophenyl)-4-methyl-4H-[1,2,4]triazolo[1,5-α]pyrimidin-7-ylidene]-amine, N-bicyclo[2.2.1]hept-2-yl-N-[5-chloro-6-(2-chloro-6-fluorophenyl)-4-methyl-4H-[1,2,4]triazolo[1,5-α]pyrimidin-7-ylidene]-amine, N-[5-chloro-6-(2,6-difluoro-4-methoxyphenyl)-4-methyl-4H-[1,2,4]triazolo[1,5-α]pyrimidin-7-ylidene]-N-(,1,1-trifluoroprop-2-yl)-amine, N-[5-chloro-6-(2,6-difluoro-4-methoxyphenyl)-4-methyl-4H-[1,2,4]triazolo[1,5-α]pyrimidin-7-ylidene]-N-(2,2,2-trifluoroethyl)-amine, N-[5-chloro-6-(2,6-difluoro-4-methoxyphnyl)-4-methyl-4H-[1,2,4]triazolo[1,5-α]pyrimidin-7-ylidene]-N-cyclopentylamine, N-(5-chloro-3-methyl-6-(2,4,6-trifluorophenyl)-3H-[1,2,4]triazolo[1,5-a,]pyrimidin-7-ylidene]-N-(2,2,2-trifluoroethyl)-amine, N-(5-chloro-3-methyl-6-(2,4,6-trifluorophenyl)-3H-[1,2,4]triazolo[1,5-α]pyrimidin-7-ylidene]-N-cyclopentylamine, N-[5-chloro-3-methyl-6-(2,4,6-trifluorophenyl)-3H-[1,2,4]triazolo[1,5-a]pyrimidin-7-ylidene]-N-(1,1,-trifluoroprop-2-yl)-amine, N-[5-chloro-3-methyl-6-(2,4,6)-trifluorophenyl)-3H-[1,2,4]triazolo[1,5-α]pyrimidin-7-ylidene]-N-isopropylamine, N-sec-butyl-N-[5-chloro-3-methyl-6-(2,4,6-trifluorophenyl)-3H-[1,2,4]triazolo[1,5-α]pyrimidin-7-ylidene]-amine, N-bicyclo[2.2.1]hept-2-yl-N-[5-chloro-3-methyl-6-(2,4,6-trifluorophenyl)-3H-[1,2,4]triazolo[1,5-α]-pyrimidin-7-ylidene]-amine, N-(5-chloro-6-(2-chloro-6-fluorophenyl)-3-methyl-3H-[1,2,4]triazolo[1,5-α]pyrimidin-7-ylidene]-N-cyclopentyl-amine, N-[5-chloro-6-(2-chloro-6-fluorophenyl)-3-methyl-3H-[1,2,4]triazolo[1,5-α]pyrimidin-7-yilidene]-N-(2,2,2-trifluorethyl)-amine, N-[5-chloro-6-fluorophenyl)-3-methyl-3H-[1,2,4]triazolo[1,5-α]pyrimidin-7-ylidene]-N-(1,1,1-trifluoroprop-2-yl)-amine, N-[5-chloro-6-(2-chloro-6-fluoro-phenyl)-3-methyl-3H-[1,2,4]triazolo[1,5-α]pyrimidin-7-ylidene]-N-isopropyl-amine, N-sec.-butyl-N-[5-chloro-6-(2-chloro-6-fluorophenyl)-3-methyl-3H-[1,2,4]triazolo[1,5-α]pyrimidin-7-ylidene]-amine, N-bicyclo[2.2.1]hept-2-yl-N-[5-chloro-6-(2-chloro-6-fluorophenyl)-3-methyl-3H-[1,2,4]triazolo[1,5-α]pyrimidin-7-ylidene]-amine, N-[5-chloro-6-(2,6-difluoro-4-methoxyphenyl)-3-methyl-3H-[1,2,4]triazolo[1,5-α]pyrimidin-7-ylidene]-N-(1,1,1-trifluoroprop-2-yl)-amine, N-[5-chloro-6-(2,6-difluoro-4-methoxyphenyl)-3-methyl-3H-[1,2,4]triazolo[1,5-α]pyrimidin-7-ylidene]-N-(2,2,2-trifluoroethyl)-amine, N-[5-chloro-6-(2,6-difluoro-4-methoxyphenyl)-3-methyl-3H-[1,2,4]triazolo[1,5-α]pyrimidin-7-ylidene]-N-cyclopentylamine.

The invention relates furthermore to a composition which consists of two compounds of formula I as defined hereinbefore, wherein
(a) one compound of formula I wherein $R^1$ is attached in the 3 position; and
(b) one compound of formula I wherein $R^1$ is attached in the 4 position.

Due to excellent activity, the compounds of formula I may be used in cultivation of all plants where infection by phytopathogenic fungi is not desired, e.g. cereals, solanaceous crops, vegetables, legumes, apples, vine.

Moreover, the compounds I are suitable for controlling harmful fungi such as Paecilomyces variotii in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

The invention further provides a fungicidal composition which comprises an active ingredient, which is at least one compound of formula I as defined above, and one or more carriers.

A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed, soil, or water in which a plant grows, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels, tablets and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be Chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or y-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand.

Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending an the nature of the compound according to general formula I to be formulated. Surfactants may also mean mixtures of individual surfactants.

The compositions of the invention may for example be formulated as wettable powders, water dispersible granules, dusts, granules, tablets, solutions, emulsifiable concentrates, emulsions, suspension concentrates and aerosols.

Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers.

Dusts are usually formulated as a dust concentrate having a similar composition to that of a wettable powder but without a dispersant, and may be diluted in the field with further solid carrier to give a composition usually containing 0.5 to 10% w/w of active ingredient.

Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents.

The so-called "dry flowables" consist of relatively small granules having a relatively high concentration of active ingredient.

Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors.

Suspension concentrates are usually milled so as to obtain a stable, nonsedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected. The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can ba added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| | Emulsion Concentrate (EC) | |
| --- | --- | --- |
| Active Ingredient | Compound of Example 1 | 30.- % (w/v) |
| Emulsifier(s) | Atlox ® 4856B/Atlox ® 4858B[1] (mixture containing calcium alkyl arylsulfonate, fatty alcohol ethoxylates and light aromatics/ mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | to 1000 ml |

| | Suspension Concentrate (SC) | |
| --- | --- | --- |
| Active Ingredient | Compound of Example 1 | 50% (w/v) |
| Dispersing agent | Soprophor ® FL[3] (polyoxyethylene polyaryl phenyl etherphosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |

| | Wettable Powder (WP) | |
| --- | --- | --- |
| Active Ingredient | Compound of Example 4 | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates) | 3% (w/w) |
| Carrier/Filler | Carrier/Filler | 35% (w/w) |

| | Water Dispersible Granules (WG) | |
| --- | --- | --- |
| Active Ingredient | Compound of Example 12 | 50% (w/w) |
| Dispersing/ Binding agent | Witcosperse ® D-450[6] (mixture of sodium salis of condensed naphthalene sulfonic acid and alkyl sulfonates) | 8% (w/w) |

| | -continued | |
|---|---|---|
| Wetting agent | Morwet ® EFW[6] (formaldehyde condensation product) | 2% (w/w) |
| Antifouling agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/Filler | Carrier/Filler | 35% (w/w) |

[1] commercially available from ICI Surfactants
[2] commercially available from Deutsche Shell AG
[3] commercially available from Rhône-Poulenc
[4] commercially available from Kelco Co.
[5] commercially available from Zeneca
[6] commercially available from Witco
[7] commercially available from International Speciality Products The compositions of this invention can be applied to the plants or their environment simultaneous with or in succession with other active substances. These other active substances can be either fertilisers, agents which donate trace elements or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfaceness or other additives which promote application.

The other fungicidal compound can be, for example, one which is also capable of combating diseases of cereals (e.g. wheat) such as those caused by Erysiphe, Puccinia, Septoria, Gibberelia and Helminthosporium spp., seed and soil borne diseases and downy and powdery mildews on vines, early and late blight an solanaceous crops, and powdery mildew and scab an apples etc. These mixtures of fungicides can have a broader spectrum of activity than the compound of general formula I alone.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride and copper sulfate, cyazofamide, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenoxanil, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, iprovalicarb, kasugamycin, KE-7281, kitazin P, kresoximmethyl, mancozeb, maneb, mepanipyrim, mepronil, metalaxyl, metconazole, methfuroxam, MON 65500, myclobutanil, neoasozin, nicket dimethyldithiocarbamate, nitrothalisopropyl, nuarimol, ofurace, organo mercury compounds,oxadixyl, oxycarboxin, penconazole, pencycuron, phenazineoxide, phthalide, picoxystrobin, polyoxin D, polyram, probenazole, prochloraz, procymidione, propamocarb, propiconazole, propineb, pyraclostrobin, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, trifloxystrobin, triflumizole, triforine, triticonazole, validamycin A, vinclozolin, XRD-563, zarilamid, zineb, ziram.

In addition, the co-formulations according to the invention may contain at least one compound of formula I and any of the following contain at least one compound of formula I and any of the following classes of biological control agents such as viruses, bacteria, nematodes, fungi, and other microorganisms which are suitable to control insects, weeds or plant diseases or to induce host resistance in the plants. Examples of such biological control agents are: *Bacillus thuringiensis, Verficillium lecanii, Autographics californica* NPV, *Beauvaria bassiana, Ampelomyces quisqualis, Bacilis subtilis, Pseudomonas chlororaphis, Pseudomonas fluorescens, Steptomyces griseoviridis* and *Trichoderma harzianum*.

Moreover, the co-formulations according to the invention may contain at least one compound of formula I and a chemical agent that induces the systemic acquired resistance in plants such as for example isonicotinic acid or derivatives thereof, 2,2-di-chloro-3,3-dimethylcyclopropanecarboxylic acid or BION.

The compounds of general formula I can be mixed with soil, pest or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent an the individual compound selected, and also a variety of external factors, such as climate, whose impact is normally mitigated by the use of a suitable formulation.

SYNTHESIS EXAMPLES

With due modification of the starting compounds, the protocols shown in the synthesis examples below were used for obtaining further compounds I. The resulting compounds, together with physical data, are listed in the Table which follows.

Example 1
Preparation of N-(5-chloro-4-methyl-6-(2,4,6-trifluorophenyl)-4H[1,2,4]triazolo[1,5-α]pyrimidin-7-ylidene]-N-(2,2,2-trifluoroethyl)-amine 1A and N-[5-chloro-3-methyl-6-(2,4,6-trifluorophenyl)-4H-[1,2,4]triazolo[1,5-α]pyrimidin-7-ylidene]-N-(2,2,2-trifluoroethyl)-amine 1B A mixture of 5-chloro-6-(2,4,6-trifluorophenyl)-7-(1,1,1trifluoroprop-2-ylamino)-triazolo[1.5-α]pyrimidine (2.5 g, 6.3 mmol, prepared according to WO-A 98/46608), dimethylformamide (15ml), potassium hydrogencarbonate (10 g) and methyliodide was stirred at ambient temperature for 45 minutes. The reaction mixture was poured into water (400 ml) and extracted with diethylether twice (300 ml). The organic Phase was separated, dried with anhydrous sodium sulphate and filtered. The filtrate was evaporated under reduced pressure and purified by flash chromatography to yield 2 g of the product as a mixture of 1A and 1B. The regioisomers were separated by colum chromatography to yield

TABLE I

| Ex. | $R^1$ | $R^2$ | $L^1$ | $L^3$ | $L^4$ | melting point (° C.) |
|---|---|---|---|---|---|---|
| 2 | 4-n-propyl | 1,1,1-trifluoroprop-2-yl | F | F | F | 105–109 |
| 3 | 4-ethyl | 1,1,1-trifluoroprop-2-yl | F | F | F | 95 |
| 4 | 4-n-propyl | 1,1,1-trifluoroprop-2-yl | F | $OCH_3$ | F | 95 |
| 5 | 4-methyl | 1,1,1-trifluoroprop-2-yl | F | H | F | 147–151 |
| 6 | 4-methyl | 1,1,1-trifluoroprop-2-yl | Cl | H | H | 151–160 |
| 7 | 4-methyl | 1,1,1-trifluoroprop-2-yl | F | F | H | 110–114 |
| 8 | 4-methyl | 2,2,2-trifluoroethyl | F | F | F | 125 |
| 9 | 3-n-propyl | 1,1,1-trifluoroprop-2-yl | F | $OC_3H_7$ | F | 155 |
| 10 | 3-ethyl | 1,1,1-trifluoroprop-2-yl | F | F | F | 138 |
| 11 | 3-n-propyl | 1,1,1-trifluoroprop-2-yl | F | F | F | 127 |
| 12 | 3-n-propyl | 1,1,1-trifluoroprop-2-yl | F | $OCH_3$ | F | 169 |
| 13 | 3-methyl | 1,1,1-trifluoroprop-2-yl | F | $OCH_3$ | F | 176–180 |
| 14 | 3-methyl | 1,1,1-trifluoroprop-2-yl | F | H | F | 172–175 |
| 15 | 3-methyl | 1,1,1-trifluoroprop-2-yl | Cl | H | H | 153–162 |
| 16 | 3-methyl | 1,1,1-trifluoroprop-2-yl | F | F | H | 159–162 |
| 17 | 4-methyl | 2,2,2-trifluoroethyl | F | F | F | 137 |

1A: 0.8 g, m.p. 112–120° C.
1B: 0.7 g, m.p. 165–167° C.

Biological Investigations
A Evaluation of In Vivo Fungicidal Activity of Test Compounds Test compounds are dissolved in acetone and diluted with deionized water (95 parts water to 5 parts acetone) containing 0.05% TWEEN 20©, a polyoxyethylene sorbitan monolaurate surfactant TWEEN 20©, a polyoxyethylene sorbitan monolaurate surfactant 200, 50 and 12.5 ppm.

The plants are sprayed with the test solutions, dried and inoculated with fungi later the same day. When disease symptom development is optimal, the plants are rated for disease control according to the rating scale shown below.

Each test contains inoculated treated plants, inoculated untreated plants and inoculated plants treated with reference fungicides. The data obtained are shown in Table II.

RATING SCALE

| Rating | Range % Control |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| t | no evaluation possible |

TARGETS

| Abbreviation | Disease | Pathogen |
|---|---|---|
| AS | Apple Scab | Venturia inaequalis |
| GDM | Grape downy mildew | Plasmopara viticola |
| PB | Pepper Botrytis | Botrytis cinera |
| RB | Rice Blast | Pyricularia grisea f. sp. oryzae |
| SBC | Sugar Beet Cercospora | Cercospora beticola |
| TEB | Tomato early blight | Alternara solani |
| WPM | Wheat powdery mildew | Blumeria graminis |

B Evaluation of in vitro Fungicidal Activity

Test compounds are dissolved in acetone to give concentrations of 25, 10 and 1 ppm and are added to individual cell Walls (24-cell-well plates, Corning), which were previously filled with a suspension of ground plates, Corning), which were previously filled with a suspension of ground fungal mycelium in a chemically defined growth medium. After 3-7 days of incubation, inhibition of mycefial growth is recorded using the following scale: The data obtained are shown in Table II.

TABLE II

RATING SCALE

| Rating | Degree of Inhibition |
|---|---|
| 0 | None |
| 3 | slight |
| 5 | moderate |
| 7 | severe |
| 9 | complete |

TARGET

| Symbol | Disease | Pathogen |
|---|---|---|
| PSDCHE | Cereal eye spot | Pseudocercosporella herpotrichoides |
| PYTHUL | Fruit rot | Pythium ultimum |
| RHIZSO | Rice sheath blight | Rhizoctonia solani |

| Ex. | Dose [ppm] | AS | GDM | PB | RB | SBC | TEB | WPM | PSDCH | PYTHU | RHIZSO |
|---|---|---|---|---|---|---|---|---|---|---|---|
| 1A | 200 | 9 | 4 | 0 | 6 | 8 | 3 | 8 | | | |
| 1A | 50 | 6 | 6 | 5 | 0 | 6 | 0 | 7 | | | |
| 1A | 12.5 | 0 | 5 | 0 | 0 | 0 | 0 | 0 | | | |

TABLE II-continued

| | | | | | | | | | | | |
|---|---|---|---|---|---|---|---|---|---|---|---|
| 1A | 25 | | | | | | | | 0 | 0 | 7 |
| 1A | 10 | | | | | | | | 0 | 0 | 7 |
| 1A | 1 | | | | | | | | 0 | 0 | 5 |
| 1B | 200 | 5 | 7 | 6 | 5 | 6 | 4 | 0 | | | |
| 1B | 50 | 4 | 0 | 0 | 0 | 6 | 2 | 0 | | | |
| 1B | 12.5 | 4 | 0 | 0 | 0 | 0 | 0 | 0 | | | |
| 1B | 25 | | | | | | | | 3 | 5 | 5 |
| 1B | 10 | | | | | | | | 1 | 1 | 5 |
| 1B | 1 | | | | | | | | 0 | 0 | 5 |
| 2 | 200 | 5 | 1 | 1 | 0 | 3 | 0 | 0 | | | |
| 2 | 50 | 0 | 2 | 1 | 0 | 0 | 0 | 0 | | | |
| 2 | 12.5 | 0 | 4 | 1 | 0 | 0 | 0 | 0 | | | |
| 3 | 200 | 6 | 4 | 0 | 5 | 0 | 0 | 3 | | | |
| 3 | 50 | 0 | 4 | 0 | 0 | 0 | 3 | 0 | | | |
| 3 | 12.5 | 0 | 0 | 2 | 0 | 0 | 3 | 0 | | | |
| 3 | 25 | | | | | | | | 1 | 0 | 5 |
| 3 | 10 | | | | | | | | 1 | 0 | 5 |
| 3 | 1 | | | | | | | | 0 | 0 | 3 |
| 4 | 50 | 0 | 0 | 0 | 0 | 0 | 0 | 0 | | | |
| 4 | 12.5 | 0 | 0 | 0 | 0 | 0 | 0 | 0 | | | |
| 4 | 3.1 | 0 | 4 | 0 | 0 | 0 | 3 | 0 | | | |
| 5 | 200 | 0 | 5 | 1 | 0 | | 0 | 6 | | | |
| 5 | 50 | 0 | 6 | 0 | 0 | | 0 | 3 | | | |
| 5 | 12.5 | 0 | 6 | 0 | 0 | | 0 | 0 | | | |
| 6 | 200 | 5 | 7 | 0 | 5 | | 0 | 5 | | | |
| 6 | 50 | 0 | 0 | 0 | 0 | | 0 | 0 | | | |
| 6 | 12.5 | 0 | 0 | 0 | 0 | | 0 | 0 | | | |
| 6 | 25 | | | | | | | | 0 | 0 | 0 |
| 6 | 10 | | | | | | | | 1 | 0 | 0 |
| 6 | 1 | | | | | | | | 0 | 0 | 0 |
| 7 | 200 | 6 | 8 | 0 | 4 | | 0 | 6 | | | |
| 7 | 50 | 0 | 0 | 0 | 0 | | 0 | 4 | | | |
| 7 | 12.5 | 0 | 0 | 2 | 0 | | 0 | 0 | | | |
| 7 | 25 | | | | | | | | 0 | 0 | 5 |
| 7 | 10 | | | | | | | | 1 | 0 | 5 |
| 7 | 1 | | | | | | | | 0 | 0 | 5 |
| 8 | 200 | 5 | 5 | 0 | 4 | | 0 | 7 | | | |
| 8 | 50 | 0 | 4 | 0 | 0 | | 0 | 4 | | | |
| 8 | 12.5 | 0 | 5 | 0 | 0 | | 2 | 2 | | | |
| 8 | 25 | | | | | | | | 0 | 0 | 7 |
| 8 | 10 | | | | | | | | 0 | 0 | 7 |
| 8 | 1 | | | | | | | | 0 | 0 | 7 |
| 9 | 200 | 6 | 3 | 2 | 4 | 8 | 9 | 7 | | | |
| 9 | 50 | 6 | 3 | 1 | 3 | 8 | 8 | 6 | | | |
| 9 | 12.5 | 0 | 5 | 2 | 0 | 8 | 6 | 2 | | | |
| 9 | 25 | | | | | | | | 5 | 0 | 7 |
| 9 | 10 | | | | | | | | 3 | 0 | 7 |
| 9 | 1 | | | | | | | | 3 | 0 | 7 |
| 10 | 200 | 6 | 0 | 0 | 6 | 6 | 5 | 0 | | | |
| 10 | 50 | 0 | 0 | 0 | 4 | 6 | 4 | 0 | | | |
| 10 | 12.5 | 0 | 0 | 4 | 0 | 3 | 0 | 0 | | | |
| 10 | 25 | | | | | | | | 0 | 5 | 5 |
| 10 | 10 | | | | | | | | 0 | 3 | 5 |
| 10 | 1 | | | | | | | | 0 | 0 | 0 |
| 11 | 200 | 7 | 3 | 0 | 4 | 3 | 0 | 0 | | | |
| 11 | 50 | 6 | 0 | 0 | 3 | 0 | 0 | 0 | | | |
| 11 | 12.5 | 0 | 0 | 0 | 0 | 0 | 0 | 0 | | | |
| 11 | 25 | | | | | | | | 0 | 1 | 0 |
| 11 | 10 | | | | | | | | 0 | 1 | 0 |
| 11 | 1 | | | | | | | | 0 | 0 | 0 |
| 12 | 200 | 0 | 0 | 0 | 0 | 0 | 0 | 0 | | | |
| 12 | 50 | 0 | 0 | 0 | 0 | 0 | 0 | 0 | | | |
| 12 | 12.5 | 0 | 0 | 0 | 0 | 0 | 0 | 0 | | | |
| 13 | 200 | 0 | 0 | 0 | 0 | | 0 | 5 | | | |
| 13 | 50 | 0 | 0 | 0 | 0 | | 0 | 3 | | | |
| 13 | 12.5 | 0 | 0 | 0 | 0 | | 0 | 0 | | | |
| 14 | 200 | 6 | 7 | 0 | 0 | | 0 | 0 | | | |
| 14 | 50 | 0 | 4 | 0 | 0 | | 0 | 0 | | | |
| 14 | 12.5 | 0 | 0 | 0 | 0 | | 0 | 0 | | | |
| 15 | 200 | 0 | 6 | 2 | 0 | | 0 | 3 | | | |
| 15 | 50 | 0 | 4 | 0 | 0 | | 0 | 0 | | | |
| 15 | 12.5 | 0 | 2 | 0 | 0 | | 0 | 0 | | | |
| 15 | 25 | | | | | | | | 0 | 0 | 3 |
| 15 | 10 | | | | | | | | 0 | 0 | 0 |
| 15 | 1 | | | | | | | | 0 | 0 | 0 |
| 16 | 200 | 6 | 7 | 0 | 0 | | 0 | 0 | | | |
| 16 | 50 | 5 | 5 | 0 | 0 | | 0 | 0 | | | |
| 16 | 12.5 | 0 | | 0 | 0 | | 0 | 0 | | | |
| 16 | 25 | | | | | | | | 0 | 7 | 7 |

TABLE II-continued

| 16 | 10   |   |   |   |   |   |   | 0 | 5 | 7 |
| 16 | 1    |   |   |   |   |   |   | 0 | 0 | 5 |
| 17 | 200  | 6 | 5 | 0 | 4 | 0 | 6 |   |   |   |
| 17 | 50   | 2 | 0 | 0 | 3 | 0 | 2 |   |   |   |
| 17 | 12.5 | 0 | 0 | 0 | 0 | 0 | 0 |   |   |   |
| 17 | 25   |   |   |   |   |   |   | 3 | 7 | 7 |
| 17 | 10   |   |   |   |   |   |   | 1 | 5 | 7 |
| 17 | 1    |   |   |   |   |   |   | 0 | 0 | 7 |

What is claim is:

1. Compounds of formula I:

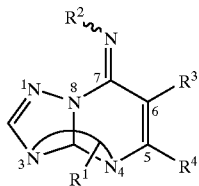

in which $R^1$ is $C_1$–$C_{10}$-alkyl, $C_1$–$C_6$-alkoxy-$C_1$–$C_6$alkyl, $C_3$–$C_8$-cycloalkyl-$C_1$–$C_6$-alkyl, $C_2$–$C_{10}$-alkenyl, $C_2$–$C_{10}$-alkynyl, $C_4$–$C_{10}$-alkadie $C_1$–$C_{10}$-fluoroalkyl, trihydrocarbylsilyl, formyl, $C_1$–$C_{10}$-alkanoyl or $C_1$–$C_{10}$-alkoxycarbonyl group being attached either to the nitrogen in the 3- or 4-position;

$R^2$ is hydrogen, $C_1$–$C_{10}$-alkyl, $C_2$–$C_{10}$-alkenyl, $C_2$–$C_{10}$-alkynyl, $C_4$–$C_{10}$-alkadienyl, $C_1$–$C_{10}$-haloalkyl, $C_3$–$C_6$-cycloalkyl, $C_8$–$C_{14}$-bicycloalkyl, phenyl, naphthyl, 5- or 6-membered heteroaryl or heterocyclic groups containing one to four nitrogen atoms or one to three nitrogen atoms and one sulfur or oxygen atom as ring members;

$R^3$ is phenyl, $C_3$–$C_6$-cycloalkyl or 5- or 6-membered heteroaryl containing besides carbon atoms one to four nitrogen atoms or one to three nitrogen atoms and one sulfur or oxygen atom as ring members;

$R^4$ is halogen, amino, $C_1$–$C_{10}$-alkoxy, $C_1$–$C_{10}$-haloalkoxy, $C_1$–$C_{10}$-alkylamino or di-$C_1$–$C_{10}$-alkylamino;

wherein the bent line indicates that the double bond may be located between the 3- and 9-position or the 4-and 9- position; and the zigzag line indicates that the groups connected may have the (E)- or (Z)-configuration;

$R^1$ to $R^4$ groups independently from one another may be unsubstituted or substituted by one to three groups $R^a$;

$R^a$ halogen, nitro, cyano, hydroxy, $C_1$–$C_6$-alkyl, $C_3$–$C_6$-cycloalkyl, $C_3$–$C_6$-cycloalkenyl, $C_1$–$C_6$-haloalkyl, $C_3$–$C_6$-halocycloalkyl, $C_1$–$C_6$-alkoxy, $C_1$–$C_6$-haloalkoxy, tri-$C_1$–$C_4$-alkylsilyl, phenyl, halo- or dihalophenyl or pyridyl.

2. Compounds of formula I:

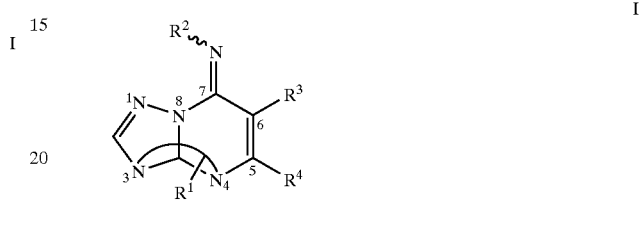

in which $R^1$ is a straight chained or branched $C_1$–$C_6$-alkyl, $C_2$–$C_6$-alkenyl or formyl, $R^2$ is hydrogen, $C_1$–$C_{10}$-alkyl, $C_2$–$C_{10}$-alkenyl, $C_2$–$C_{10}$-alkynyl, $C_4$–$C_{10}$-alkadienyl, $C_1$–$C_{10}$-haloalkyl, $C_3$–$C_6$-cycloalkyl, $C_8$–$C_{14}$-bicycloalkyl, phenyl, naphthyl, 5- or 6-membered heteroaryl or heterocyclic groups containing one to four nitrogen atoms or one to three nitrogen atoms and one sulfur or oxygen atom as ring members;

$R^3$ is phenyl, $C_3$–$C_6$-cycloalkyl or 5- or 6-membered heteroaryl containing besides carbon atoms one to four nitrogen atoms or one to three nitrogen atoms and one sulfur or oxygen atom as ring members;

$R^4$ is halogen, amino, $C_1$–$C_{10}$-alkoxy, $C_1$–$C_{10}$-haloalkoxy, $C_1$–$C_{10}$-alkylamino or di-$C_1$–$C_{10}$-alkylamino;

wherein the bent line indicates that the double bond may be located between the 3- and 9-position or the 4- and 9-position; and the zigzag line indicates that the groups connected may have the (E)- or (Z)-configuration;

$R^1$ to $R^4$ groups independently from one another may be unsubstituted or substituted by one to three groups $R^a$;

$R^a$ halogen, nitro, cyano, hydroxy, $C_1$–$C_6$-alkyl, $C_3$–$C_6$-cycloalkyl, $C_3$–$C_6$-cycloalkenyl, $C_1$–$C_6$-haloalkyl, $C_3$–$C_6$-halocycloalkyl, $C_1$–$C_6$-alkoxy, $C_1$–$C_6$-haloalkoxy, tri-$C_1$–$C_4$-alkylsilyl, phenyl, halo- or dihalophenyl or pyridyl.

3. Compounds of formula I according to claim 1 in which $R^2$ represents a straight chained or branched $C_1$–$C_6$-alkyl, $C_1$–$C_6$-haloalkyl, $C_3$–$C_8$-cycloalkyl, $C_5$–$C_8$-bicycloalkyl or $C_2$–$C_6$-alkenyl.

4. Compounds of formula I according to claim 1 in which $R^3$ represents optionally substituted phenyl.

5. Compounds of formula I according to claim 1 in which $R^4$ represents halogen.

6. Compounds of formula I according to claim 1 in which $R^3$ is an optionally substituted phenyl group of formula:

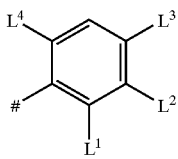

wherein # denotes the bond to the triazolopyrimidino ring and $L^1$ is fluoro, $L^2$ is hydrogen or fluoro, $L^3$ is hydrogen or fluoro or methoxy and $L^4$ is hydrogen, fluoro or chloro.

7. A process for the preparation of compounds of formula I as defined in claim 1 which comprises treating compounds of formula II:

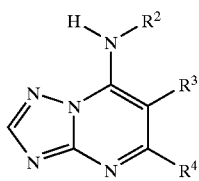

in which $R^2$, $R^3$ and $R^4$ are as defined in claim 1; with an alkylation agent of formula III:

$$R^1\text{—}X \qquad \text{III}$$

in which $R^1$ is as defined in claim 1, and X represents a leaving group, in the presence of a base or a buffer system.

8. A fungicidal mixture of a first and a second compound of formula I defined in claim 1 wherein in the first compound $R^1$ is at the 3-position, and in the second compound $R^1$ is at the 4-position.

9. A fungicidal composition which comprises a carrier and a fungicidal effective amount of at least one compound of formula I as defined in claim 1.

10. A method for controlling harmful fungi, which comprises treating fungi or the materials, plants, the soil or the seed to be protected against fungal attack with a fungicidal composition as claimed in claim 9.

* * * * *